United States Patent
Lee et al.

(10) Patent No.: US 7,858,761 B2
(45) Date of Patent: Dec. 28, 2010

(54) 1-α-HALO-2,2-DIFLUORO-2-DEOXY-D-RIBOFURANOSE DERIVATIVES AND PROCESS FOR THE PREPARATION THEREOF

(75) Inventors: Jaeheon Lee, Kyungki-do (KR); Gha-Seung Park, Kyungki-do (KR); Moonsub Lee, Daejeon (KR); Han Kyong Kim, Kyungki-do (KR); Hyo-Jeong Bang, Kyungki-do (KR); Young-Kil Chang, Seoul (KR); Gwan Sun Lee, Seoul (KR)

(73) Assignee: Hanmi Pharm. Co., Ltd, Kyungki-Do (KR)

( * ) Notice: Subject to any disclaimer, the term of this patent is extended or adjusted under 35 U.S.C. 154(b) by 988 days.

(21) Appl. No.: 11/572,790

(22) PCT Filed: Jun. 21, 2005

(86) PCT No.: PCT/KR2005/001922

§ 371 (c)(1),
(2), (4) Date: Jan. 26, 2007

(87) PCT Pub. No.: WO2006/011713

PCT Pub. Date: Feb. 2, 2006

(65) Prior Publication Data

US 2007/0238865 A1    Oct. 11, 2007

(30) Foreign Application Priority Data

Jul. 29, 2004  (KR) .................. 10-2004-0059623
May 17, 2005  (KR) .................. 10-2005-0041278

(51) Int. Cl.
*C07H 23/00* (2006.01)
*C07H 11/04* (2006.01)
*C07H 5/02* (2006.01)

(52) U.S. Cl. .................. 536/17.1; 536/4.1; 536/18.4; 536/18.5; 514/25; 549/477

(58) Field of Classification Search ............. 536/17.1, 536/4.1, 18.4, 18.5; 549/477; 514/25
See application file for complete search history.

(56) References Cited

U.S. PATENT DOCUMENTS

| 4,526,988 A * | 7/1985 | Hertel .................. 549/313 |
| 5,252,756 A | 10/1993 | Chou et al. |
| 5,401,861 A | 3/1995 | Chou et al. |
| 5,453,499 A * | 9/1995 | Chou et al. .................. 536/122 |
| 5,744,597 A | 4/1998 | Chou et al. |
| 5,945,547 A | 8/1999 | Chou et al. |

FOREIGN PATENT DOCUMENTS

| EP | 0 450 585 A2 | 10/1991 |
| EP | 0 576 231 A1 | 12/1993 |
| JP | 5-97885 A | 4/1993 |
| JP | 6-056863 A | 3/1994 |
| JP | 2003-055364 A | 2/2002 |

OTHER PUBLICATIONS

Corey, E.J., et al., "New Reagents for Stereoselective Carbonyl Reduction. An Improved Synthetic Route to the Primary Prostaglandins," J. Am Chem Society, 93:6, Mar. 24, 1971, pp. 1491-1493.
Canadian Intellectual Property, Office Action dated Nov. 24, 2008.
Japanese Office Action from counterpart application No. 2007-523465 dated Aug. 31, 2010.

* cited by examiner

*Primary Examiner*—Shaojia Anna Jiang
*Assistant Examiner*—Michael C Henry
(74) *Attorney, Agent, or Firm*—Sughrue Mion, PLLC

(57) ABSTRACT

1-α-halo-2,2-difluoro-2-deoxy-D-ribofuranose derivative of formula (I) having the 3-hydroxy group protected with a biphenylcarbonyl group is a solid which can be easily purified by a simple procedure such as recrystallization, and therefore, it can be advantageously used as an intermediate in the preparation of gemcitabine in a large scale. Further, the 1-α-halo-2,2-difluoro-2-deoxy-D-ribofuranose derivative of formula (I) can be prepared with high stereoselectivity using the compound of formula (V) as an intermediate.

12 Claims, No Drawings

1-α-HALO-2,2-DIFLUORO-2-DEOXY-D-RIBOFURANOSE DERIVATIVES AND PROCESS FOR THE PREPARATION THEREOF

FIELD OF THE INVENTION

The present invention relates to a novel 1-α-halo-2,2-difluoro-2-deoxy-D-ribofuranose derivative, and a process for the preparation thereof which is useful as an intermediate in the production of gemcitabine.

BACKGROUND OF THE INVENTION

Gemcitabine of formula (A), a medicament for treating non-small cell lung cancer (NSCLC), is a synthetic nucleoside analogue having a cytosine nucleobase stereochemically oriented upward to the β-direction at C-1 of the ribofuranose backbone.

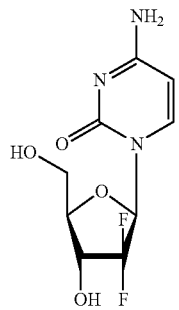

(A)

Gemcitabine may be conventionally prepared from a lactol compound as shown in Reaction Scheme 1 via an activated ribofuranose intermediate having a reactive leaving group:

Reaction Scheme 1

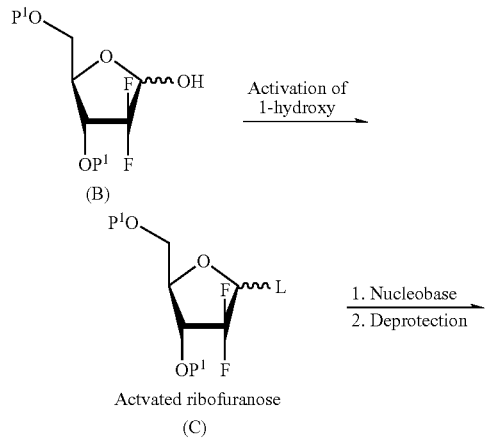

wherein, $P^1$ is a hydroxy protecting group, and L is a leaving group.

Specifically, gemcitabine may be prepared by 1a) introducing a reactive leaving group (L) into C-1 of the ribofuranose ring of a lactol compound (B) to obtain an activated ribofuranose intermediate (C), and 1b) glycosylating the compound of formula (C) with cytosine to form an N-glycosidic bond.

In Reaction Scheme 1, glycosylation step 1b) undergoes via a bimolecular ($S_N2$) mechanism of nucleophilic substitution, and thus, it is important in the preparation of gemcitabine to obtain a high purity α-anomer of the compound (C) having the leaving group (L) oriented down. Accordingly, many attempts have been made to develop a process for stereoselectively introducing a leaving group (L) into C-1 of the ribofuranose ring of the lactol compound (B).

For example, U.S. Pat. Nos. 4,526,988 and 5,453,499 disclose an activated ribofuranose intermediate such as 1-α-halo-ribofuranose having a halo leaving group introduced at C-1 of the ribofuranose ring. Specifically, U.S. Pat. No. 4,526,988 describes a method for preparing a 1-α-halo-ribofuranose derivative of formula (F) by 2a) reacting the 1-hydroxy group of a lactol compound of formula (D) with an acetyl source such as acetic anhydride to obtain a 1-acetate derivative of formula (E), and 2b) reacting the 1-acetate derivative of formula (E) with gaseous HBr or HCl to obtain a 1-halo ribofuranose, as shown in Reaction Scheme 2:

Reaction Scheme 2

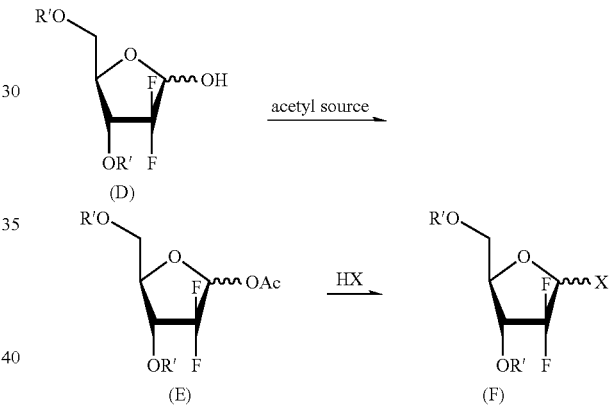

wherein, R' is a hydroxy protecting group, Ac is acetyl, and X is Br or Cl.

However, this process gives a low yield of the desired α-halo anomer due to its low stereoselectivity.

U.S. Pat. No. 5,453,499 discloses a process for preparing an α-enriched 1-halo ribofuranose of formula (H) having an α:β ratio of 9:1 to 10:1 by reacting a β-sulfonate compound of formula (G) with a halide source in an inert solvent, as shown in Reaction Scheme 3:

Reaction Scheme 3

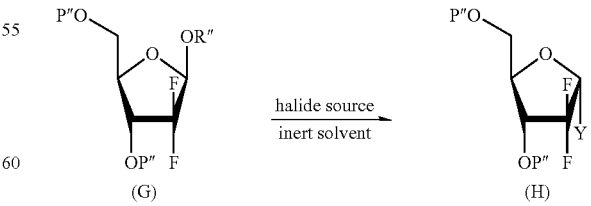

wherein, P" is a hydroxy protecting group such as benzoyl, R" is sulfonate, and Y is halogen.

However, the 1-sulfonate compound of formula (G) used as a starting material in this process, prepared via a lactol compound by the method described in U.S. Pat. No. 5,401,861, has an α:β ratio of about 1:4, and therefore, the overall stereoselectivity (α:β) ratio for the 1-halo anomer is only about 3:1.

Further, the prior 1-α-halo-furanoses having the 3- and 5-hydroxy groups protected, e.g., by benzoyl groups, exist in an oily state which is more difficult to handle and store than a solid form, besides the fact that an uneconomical column chromatography process is required for its isolation from a mixture of α- and β-anomers. Therefore, there has been a need to develop an improved process for preparing gemcitabine using an α-halo-furanose as an intermediate.

SUMMARY OF THE INVENTION

Accordingly, it is a primary object of the present invention to provide a novel 1-α-halo-D-ribofuranose derivative in a solid form, which can be purified using a simple purification procedure such as recrystallization suitable for mass-production.

It is another object of the present invention to provide a highly stereoselective method for preparing said compound in a high purity and yield.

It is still another object of the present invention to provide a compound which can be used as an intermediate in said method.

In accordance with one aspect of the present invention, there is provided a 1-α-halo-2,2-difluoro-2-deoxy-D-ribofuranose derivative of formula (I) in a solid form:

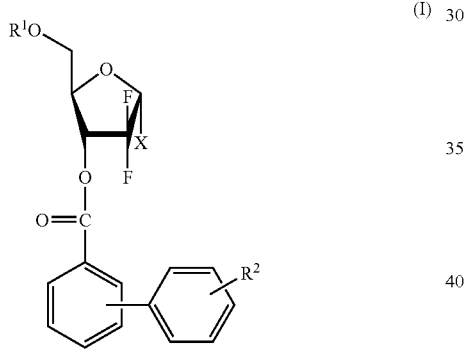

(I)

wherein,
$R^1$ is benzoyl or

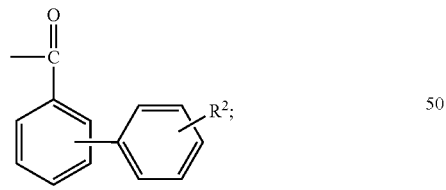

$R^2$ is hydrogen, cyano, halogen, carboalkoxy, nitro, $C_{1-2}$ alkoxy, $C_{1-2}$ alkyl or dialkylamino; and
X is Cl, Br or I.

In accordance with another aspect of the present invention, there is provided a method for preparing the 1-α-halo-2,2-difluoro-2-deoxy-D-ribofuranose derivative of formula (I), comprising the steps of (i) reducing a 1-oxoribose compound of formula (II) to obtain a lactol compound of formula (III);

(ii) reacting the compound of formula (III) with a halophosphate compound of formula (IV) in the presence of a base to obtain a 1-phosphate furanose derivative of formula (V); and (iii) reacting the compound of formula (V) with a halide source, followed by recrystallizing the resulting product to obtain the 1-α-halo-2,2-difluoro-2-deoxy-D-ribofuranose derivative of formula (I):

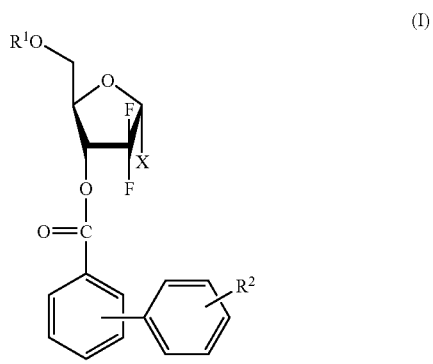

(I)

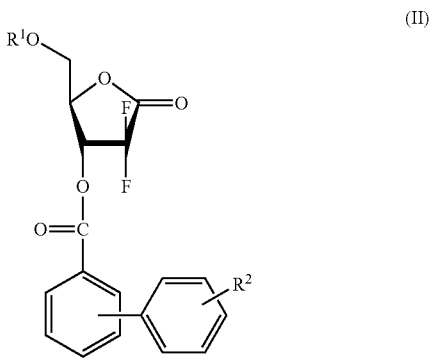

(II)

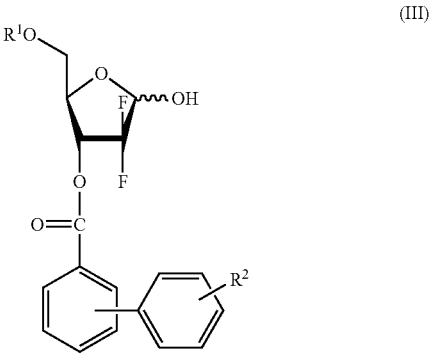

(III)

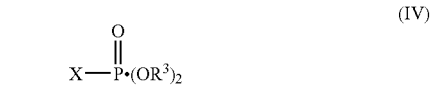

(IV)

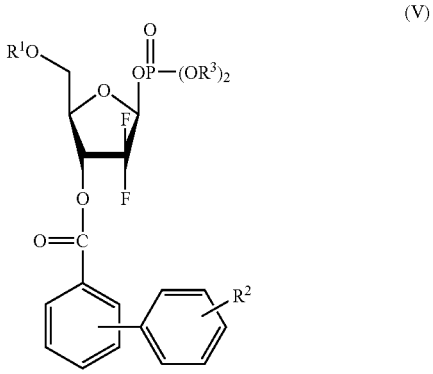

(V)

wherein, $R^1$, $R^2$ and X have the same meanings as defined above; and $R^3$ is methyl, ethyl or phenyl, preferably phenyl.

In accordance with still another aspect of the present invention, there is provided a novel 1-phosphate furanose derivative of formula (V) which can be advantageously used as an intermediate in the preparation of the 1-α-halo-D-ribofuranose derivative of formula (I):

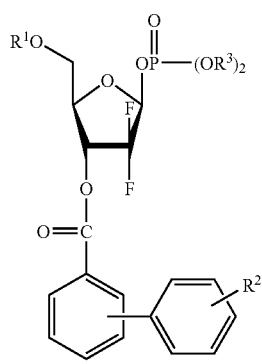

(V)

wherein, $R^1$, $R^2$ and $R^3$ have the same meanings as defined above.

DETAILED DESCRIPTION OF THE INVENTION

The term "anomer-enriched" used herein means an anomer mixture having a specific anomer content of greater than 50%, preferably a substantially pure anomer.

Among the compounds of formula (I) of the present invention, preferred are those wherein $R^2$ is hydrogen.

The inventive ribofuranose derivative of formula (I) is characterized by having a 3-hydroxy group protected with a biphenylcarbonyl group. Also, the inventive derivative may have a biphenylcarbonyl group as the 5-hydroxy protecting group.

Thus, the inventive 1-α-halo ribofuranose derivative can be obtained as a solid and, accordingly, it can be easily purified in a high purity of 99.5% or more by a simple purification procedure such as recrystallization.

Also, the inventive 1-α-halo-ribofuranose derivative of formula (I) may be coupled with cytosine by a conventional glycosylation reaction to prepare gemcitabine having the cytosine moiety at C-1 of the ribofaranose ring oriented up (β-configuration).

In the preparation of gemcitabine via glycosylation step using a 1-halo ribofuranose derivative, the purity of the α-halo anomer is very important. If the content of the β-halo anomer increases, the stereoselectivity of the glycosylation reaction markedly decreases, leading to a low yield of the desired β-nucleoside, gemcitabine.

Accordingly, gemcitabine having a high β/α-anomer ratio of 4 to 14, which is markedly higher relatively to the conventional methods (a β-/α-anomer ratio is 2 to 3) may be prepared effectively by performing glycosylation using the inventive α-halo compound.

The inventive method for preparing the 1-α-halo furanose derivative of formula (I) is described in Reaction Scheme 4.

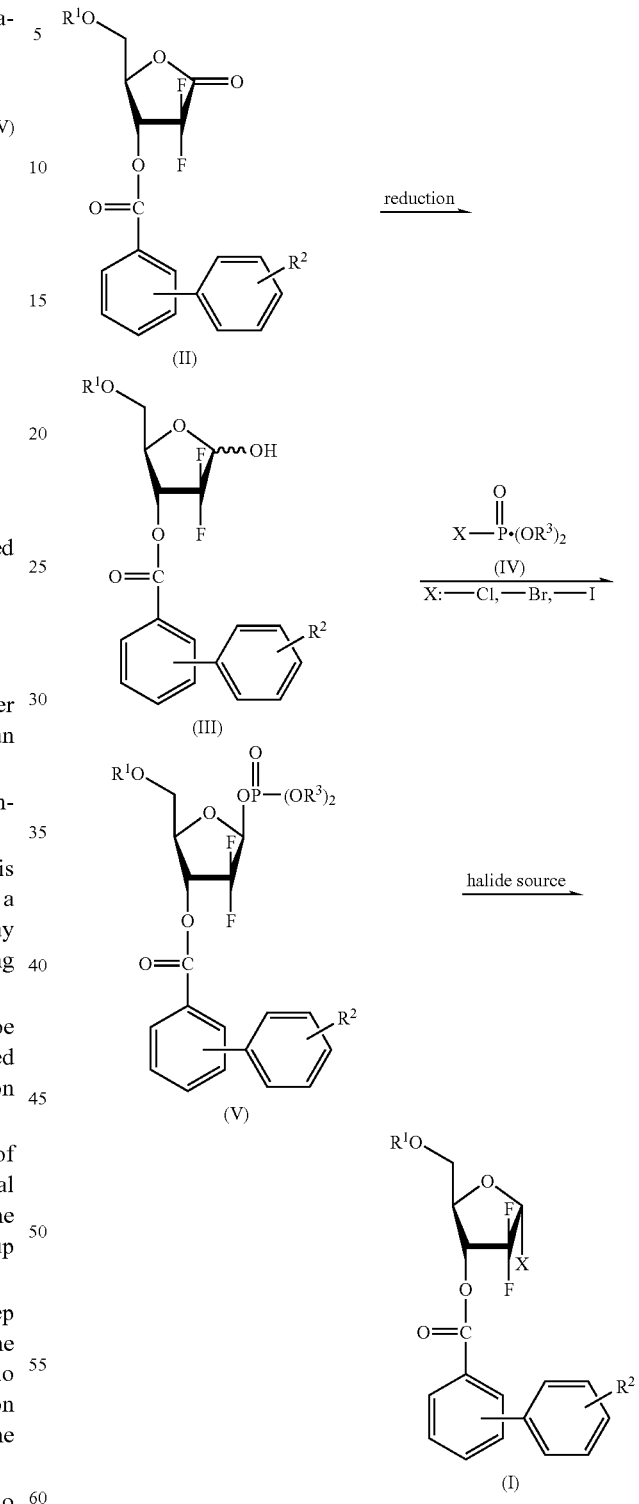

wherein, $R^1$, $R^2$, $R^3$ and X have the same meanings as defined above.

In Reaction Scheme 4, the 1-halo-2,2-difluoro-2-deoxy-D-ribofuranose derivative of formula (I) may be prepared in a form having an high α-anomer content of 99.5% or more by (i) reducing the 1-oxoribose compound of formula (II)

according to a conventional method to obtain the lactol compound of formula (III), a mixture of α- and β-anomers; (ii) reacting the compound of formula (III) with a halo phosphate compound of formula (IV) in the presence of a base to obtain the β-enriched 1-phosphate furanose of formula (V) having a β/α ratio of 10 or more; and (iii) reacting the compound of formula (V) with a halide source to obtain the compound of formula (I).

The use of the novel furanose intermediates of formula (V) having a phosphate leaving group is the unique feature of the inventive method for preparing the 1-halo ribofuranose of formula (I) having a high α-anomer content.

Thus, in step (ii) for preparing the phosphate furanose of formula (V) from the lactol compound of formula (III), the β-phosphate anomer can be obtained with a high β/α ratio of greater than 10. Also, the subsequent step (iii) can be performed continuously without isolating the intermediate to obtain the α-halo furanose of formula (I) with a high a/p ratio of at least 10.

Further, in accordance with the present invention, the α-halo-furanose is obtained as a solid when a biphenylcarbonyl group is adopted as the 3- and/or 5-hydroxy protecting groups of the ribofuranose ring, and the solid form can be easily purified to an enantiomer purity of 99.5% or more using a simple purification process, which makes it possible to prepare the desired β-nucleoside having a high β/α ratio of 4 to 14. Such a high β/α ratio is markedly higher than the β/α ratio of 2 to 3 achievable in the conventional methods.

Specifically, in step (i) of the Reaction Scheme 4, the lactol compound of formula (III) may be prepared by reducing the compound of formula (II) with a reducing agent, as described in U.S. Pat. Nos. 4,526,988 and 5,464,826. The 1-oxoribose compound of formula (II) used as the starting material in step (i) may be prepared by a method comprising the steps of protecting the 3-hydroxy group of a compound of formula (VI) with a biphenylcarbonyl protecting group, followed by hydrolyzing the resulting product in the presence of a base to obtain a 3R-carboxylate enantiomer of formula (VII):

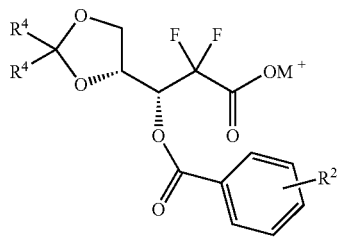

wherein, $R^2$ has the same meaning as defined above, $R^4$ is methyl or ethyl, $R^5$ is $C_{1-3}$ alkyl, and M is $NH_4$, sodium or potassium.

The solvent suitable for use in step (i) is tetrahydrofuran, diethyl ether or dioxane; and the reducing agent may be lithium aluminum hydride, diisobutyl aluminum hydride or lithium tri-tert-butoxyaluminohydride, preferably lithium tri-tert-butoxyaluminohydride; and the reduction may be conducted at room temperature for 1 to 2 hours after the addition of the reducing agent at −50 to −20° C.

In this reduction step (i), the lactol compound of formula (III) is obtained as a 1:1 to 2:1 mixture of α- and β-anomers; and the next step (ii) may be conducted after isolating each anomer obtained in step (i), or conducted as is without such an isolating process.

In step (ii), the 1-phosphate furanose of formula (V) may be prepared by reacting the compound of formula (III) with the halophosphate compound of formula (IV) in the presence of a base to obtain the β-enriched compound of formula (V) having a β/α ratio of 10 or more. In this step, the phosphate leaving group used may be dimethylphosphate, diethylphosphate, or diphenylphosphate, preferably diphenylphosphate.

Step (iii) may be conducted after isolating the desired β-anomer obtained in step (ii) by recrystallization using a solvent such as water, ethanol, propanol, isopropanol, n-butanol, ethyl acetate and a mixture thereof, preferably isopropanol or a water-isopropanol mixture. This step may also be conducted with the crude product of step (ii) without such an isolating process.

The halophosphate compound of formula (IV) may be used in an amount ranging from 1.1 to 1.5 molar equivalents based on the lactol compound of formula (III). The compound of formula (IV) is commercially available or may be easily prepared in accordance with the conventional procedures disclosed in *Biochem. Preps.*, 1, 50 (1951) or *J. Chem. Soc.*, 2921 (1949). Step (ii) can be facilitated by the addition of a catalyst such as 4-dimethylaminopyridine or 4-pyrrolidinopyridine.

Also, the base used for neutralizing the acid produced in step (ii) may be selected from the group consisting of pyridine, triethylamine, tributylamine, diisopropylethylamine and methylpiperidine, preferably triethylamine, which may be used in an amount ranging from 1.2 to 2.0 molar equivalents based on the lactol compound of formula (III). The solvent used in step (ii) may be benzene, toluene, acetonitrile, tetrahydrofuran, ethyl acetate, methylene chloride or chloroform, preferably toluene, and which is carried out at −25 to 50° C. for 2 to 10 hours.

Further, in step (iii), the highly pure α-anomer of formula (I) of 99.5% or more (i.e., the β-anomer content of less than 0.5%) may be obtained by reacting the 1-phosphate furanose of formula (V) with a halide source, followed by recrystallizing the resulting product.

The halide source which can be used in step (iii) includes HCl/acetic acid, HBr/acetic acid, HBr/propionic acid, a trialkylsilyl halide, a lithium halide, a sodium halide, a cesium halide, a potassium halide, tetraalkylammonium halide and a mixture thereof; among which 30% HBr/acetic acid, 30% HBr/propionic acid, tetrabutylammonium iodide, tetrabutylammonium bromide, trimethylsilyl iodide, trimethylsilyl bromide, trimethylsilyl chloride and a trimethylsilyl chloride-lithium bromide mixture are preferred. Such a halide source is employed in an amount ranging from 5 to 30 molar equivalents, preferably from 10 to 20 molar equivalents, based on the compound of formula (V).

In case of using 1.0 M HCl/acetic acid, 30% HBr/acetic acid or 30% HBr/propionic acid as the halide source, it is used as a neat state, while the other halide sources may be used in a form diluted with a solvent such as methylene chloride, dibromoethane, dichloroethane, chloroform, THF, 1,4-dioxane, acetonitrile, N,N-dimethylformamide or N,N-dimethylacetamide.

Step (iii) may be conducted in a solvent such as methylene chloride, dibromoethane, dichloroethane or chloroform at a temperature in the range of 0 to 50° C., preferably 10 to 30° C. for 30 minutes to 24 hours.

The resulting 1-halo ribofuranose is a mixture of α- and β-anomers having an α/β ratio of at least 10 and the desired α-halo anomer may be isolated form the mixture by recrystallization using a solvent such as methanol, ethanol, isopropanol, acetonitrile, water or a mixture thereof, preferably isopropanol or a isopropanol-water mixture, to obtain the 1-α-halo ribofuranose in a high purity of 99.5% or more.

The inventive method for preparing the 1-α-halo furanose of formula (I) using the 1-phosphate furanose of formula (V) as an intermediate gives a total yield of 65 to 75%, which is markedly higher than that achievable by the conventional method (total yield of about 45%).

The following Preparations and Examples are given for the purpose of illustration only and are not intended to limit the scope of the invention.

In the following Preparation Examples and Examples, the term "—OCOBiPh" or "BiPhOCO—" refers to

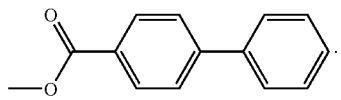

HPLC analyses for the compound of formula (V) was performed with a YMC pack pro C18 RS (4.6×150 mm, 5 μm) column using a mixture of buffer and methanol (17:83, v/v) as an eluent; and the compound of formula (I), with a Capcell-pak MG C18 RS (4.6×150 mm, 5 μm) column using a mixture of a buffer and methanol (1:4, v/v) as an eluent. The buffer was prepared by mixing 13.8 g of $NaH_2PO_4$ and 1 L of distilled water, and adding $H_3PO_4$ thereto until pH 2.5.

Preparation Example 1

Preparation of D-erythro-2-deoxy-2,2-difluoro-pentofuranos-1-ulose-5-benzoyl-3-(4-phenyl)benzoate (Compound of Formula (II))

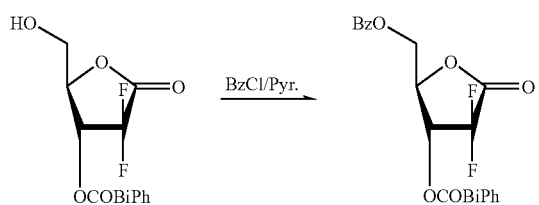

15 g of D-erythro-2-deoxy-2,2-difluoro-pentofuranos-1-ylose-3-(4-phenyl)benzoate was dissolved in 150 ml of methylene chloride, and 6.9 ml of pyridine was added dropwise thereto while stirring. 7.4 ml of benzoyl chloride dissolved in 40 ml of methylene chloride was slowly added thereto while keeping the temperature at 5 to 10° C., followed by stirring for 7 hrs at room temperature. The resulting mixture was neutralized with 105 ml of 1N HCl, and water was added thereto. The organic layer was separated, washed successively with 100 ml of saturated sodium bicarbonate and 100 ml of saline, dried over anhydrous $MgSO_4$, filtered, and concentrated under a reduced pressure. The resulting residue was recrystallized from diethyl ether/hexane (5:1, v/v), to obtain 16.8 g of the titled compound as a white solid (yield: 86%).

$^1$H-NMR (300 MHz, $CDCl_3$): 4.90~4.75 (ddd, 2H), 5.10 (dd, 1H), 5.87 (ddd, 1H), 7.65~7.50 (m, 5H), 7.78~7.67 (m, 3H), 7.81 (d, 2H), 8.13 (d, 2H), 8.23 (d, 2H)

m.p.: 130~131° C.

Preparation Example 2

Preparation of D-erythro-2-deoxy-2,2-difluoro-pentofuranos-1-ylose-3,5-di-(4-phenyl)benzoate (Compound of Formula (II))

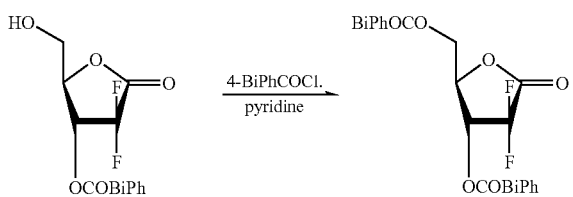

20 g of D-erythro-2-deoxy-2,2-difluoro-pentofuranos-1-ylose-3-(4-phenyl)benzoate was dissolved in 300 ml of chloroform, and 9.5 ml of pyridine was added dropwise thereto while stirring. 10.1 ml of benzoyl chloride dissolved in 55 ml of chloroform was slowly added thereto, followed by stirring for 6 hrs at room temperature. The resulting mixture was neutralized with 140 ml of 1N HCl, washed successively with 150 ml of water, 150 ml of saturated sodium bicarbonate and 150 ml of saline. The organic layer was separated, dried over anhydrous $MgSO_4$, and concentrated under a reduced pressure. The resulting residue was recrystallized from ethyl acetate/hexane (3:1, v/v), to obtain 21.8 g of the titled compound as a white solid (yield: 72%).

$^1$H-NMR (300 MHz, $CDCl_3$): 4.72~4.79 (m, 2H), 5.03 (q, 1H), 5.84~5.76 (m, 1H), 7.48~7.44 (m, 6H), 7.72~7.60 (m, 8H), 8.15~8.07 (m, 4H)

m.p.: 137~139° C.

Example 1

Preparation of 1-α-bromo-2-deoxy-2,2-difluoro-D-ribofuranosyl-5-benzoyl-3-(4-phenyl)benzoate (the compound of formula (I); $R^1$=benzoyl and $R^2$=H)

Step 1) Preparation of 2-deoxy-2,2-difluoro-D-ribofuranosyl-3-benzoyl-5-(4-phenyl)benzoate (the Compound of Formula (III))

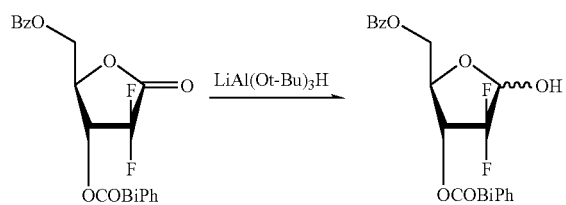

13.5 g of lithium tri-tert-butoxyaluminohydride was dissolved in 160 ml of THF and stirred for 30 minutes at room temperature, followed by cooling to −40° C. The compound obtained in Preparation Example 1 dissolved in 80 ml of THF was added thereto, the mixture was slowly warmed to room temperature, and allowed to react at that temperature for 2 hrs. Upon the completion of the reaction, 220 ml of 1N HCl was added dropwise to the reaction mixture to decompose excess lithium tri-tert-butoxyaluminohydride. The organic (THF) and aqueous layers were separated and the aqueous layer was extracted with 220 ml of diethyl ether. The ether extract was combined with the THF layer and washed successively with 220 ml of water, 220 ml of saturated sodium bicarbonate and 220 ml of saturated saline. The organic layer was separated, dried over anhydrous $MgSO_4$, and concentrated under a reduced pressure. The resulting residue was purified by flash chromatography to obtain 18.3 g of the titled compound as a primrose yellow syrup (yield: 91%).

$^1$H-NMR (300 MHz, $CDCl_3$): 3.89~3.91 (d, 1H), 4.61~4.81 (m, 2H), 5.31~5.92 (m, 2H), 7.26~7.70 (m, 10H), 8.05~8.16 (m, 4H)

Step 2) Preparation of 2-deoxy-2,2-difluoro-D-ribofuranosyl-3-benzoyl-5-(4-phenyl)benzoyl-1β-diphenylphosphate (the Compound of Formula (V))

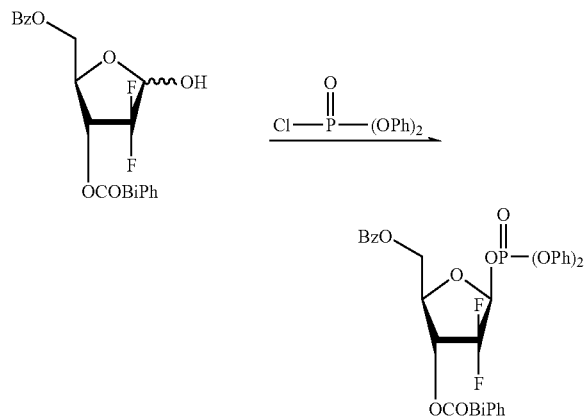

18.3 g of the compound obtained in Step 1 was dissolved in 146 ml of toluene, and 6.7 ml of triethylamine was added thereto. To the mixture, 12.4 ml of diphenylchlorophosphate dissolved in 37 ml of toluene was added dropwise, followed by stirring 4 hrs at room temperature. Upon the completion of the reaction, the residual triethylamine was neutralized by adding 48 ml of 1N HCl, the toluene and aqueous layers were separated and the aqueous layer was extracted with 48 ml of diethyl ether. The ether extract was combined with the toluene layer and washed successively with water, saturated sodium bicarbonate and saturated saline. The organic layer was separated, dried over anhydrous $MgSO_4$, and concentrated under a reduced pressure to obtain a mixture of α- and β-phosphate as a solid. The mixture was examined by $^1$H-NMR and found that the α-phosphate:β-phosphate ratio was 1:10.6. The β-phosphate was selectively recrystallized from isopropanol/water (3:1, v/v) to obtain 26.5 g of the titled compound as a white solid (yield: 87%).

$^1$H-NMR (300 MHz, $CDCl_3$): 4.56-4.25 (m, 3H), 5.80 (m, 1H), 5.95 (t, 1H), 7.44-6.98 (m, 16H), 7.51 (d, 2H), 7.57 (d, 2H), 7.89 (d, 2H), 8.01 (d, 2H)

m.p.: 101~103° C.

HPLC purity (area %): α-phosphate anomer 1.76%, β-phosphate anomer 98.24%

Step 3) Preparation of 1-α-bromo-2-deoxy-2,2-difluoro-D-ribofuranosyl-3-benzoyl-5-(4-phenyl)benzoate (the compound of formula (I))

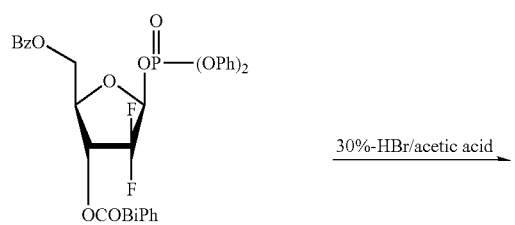

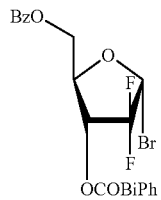

22.8 g of the compound obtained in Step 2 was added to 80.5 ml of 30% HBr/acetic acid followed by stirring for 6 hrs at room temperature. Upon the completion of the reaction, the resulting mixture was diluted with 400 ml of methylene chloride and poured over 500 ml of ice/water. The organic layer was separated, washed successively with ice water, saturated sodium bicarbonate and saline, dried over anhydrous $MgSO_4$, and concentrated under a reduced pressure to obtain a mixture of α- and β-bromo anomers as a solid. The mixture was examined by $^1$H-NMR and found that the α-bromo:β-bromo ratio was 10.7:1. The α-bromo compound was selectively recrystallized from isopropanol to obtain 17.0 g of the titled compound as a white solid (yield: 82%).

$^1$H-NMR (300 MHz, $CDCl_3$): 8.19 (d, 2H), 8.06 (d, 2H), 7.73 (d, 2H), 7.63 (d, 2H), 7.64-7.41 (m, 6H), 6.56 (d, 1H), 5.60 (dd, 1H)

m.p.: 111~112° C.

HPLC purity (area %): α-bromo anomer 99.74%, β-bromo anomer 0.26%

Example 2

Preparation of 1-α-bromo-2-deoxy-2,2-difluoro-D-ribofuranosyl-3,5-di-(4-phenyl)benzoate (the compound of formula (I); $R^1$=4-biphenylcarbonyl and $R^2$=H)

Step 1) Preparation of 2-deoxy-2,2-difluoro-D-ribofuranosyl-3,5-di-(4-phenyl)benzoate (the Compound of Formula (III))

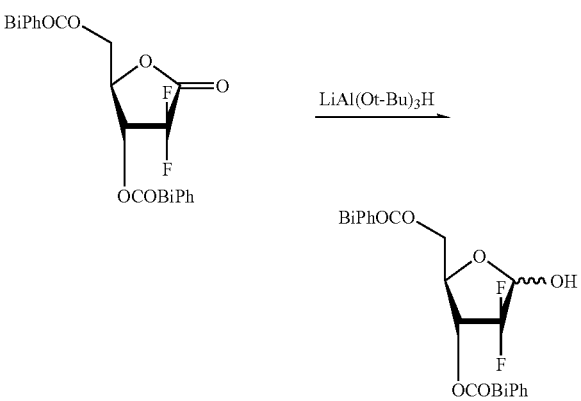

8.66 g of lithium tri-tert-butoxyaluminohydride was dissolved in 120 ml of THF and stirred for 30 minutes at room temperature, followed by cooling to −40° C. The compound obtained in Preparation Example 2 dissolved in 100 ml of THF was added thereto and stirred for 1 hr at room temperature. Upon the completion of the reaction, 142 ml of 1N HCl was slowly added dropwise to the reaction mixture to decompose excess lithium tri-tert-butoxyaluminohydride, the THF and aqueous layers were separated, and the aqueous layer was extracted with 150 ml of diethyl ether. The ether extract was combined with the THF layer, and washed successively with water, saturated sodium bicarbonate and saline. The organic layer was separated, dried over anhydrous MgSO$_4$, and concentrated under a reduced pressure. The residue was recrystallized from toluene to obtain 13.4 g of the titled compound as a white solid (yield: 89%).

$^1$H-NMR (300 MHz, CDCl$_3$): 3.45 (s, 1H), 3.8 (s), 4.85~4.50 (m, 3H), 5.8~5.4 (m, 2H), 7.49~7.43 (m, 6H), 7.71~7.61 (m, 8H), 8.18~8.12 (m, 4H)

m.p.: 156-158° C.

Step 2) Preparation of 2-deoxy-2,2-difluoro-D-ribofuranosyl-3,5-di-(4-phenyl)benzoyl-1β-diphenylphosphate (the Compound of Formula (V))

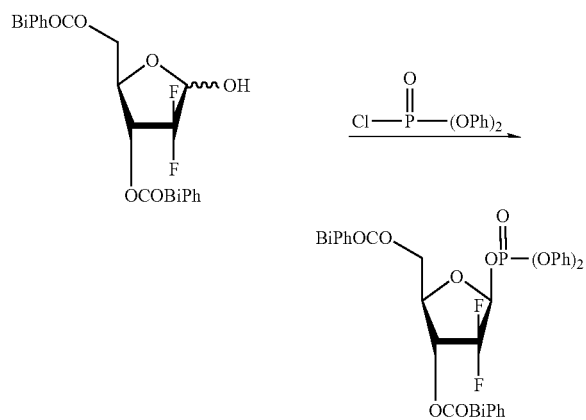

13 g of the compound obtained in Step 1 was dissolved in a mixture of 130 ml of toluene and 100 ml of methylene chloride, and 5.1 ml of triethylamine was added thereto. 7.6 ml of diphenylchlorophosphate was added dropwise to the resulting mixture and stirred for 5 hrs at room temperature. Upon the completion of the reaction, the solvent was removed under a reduced pressure, the resulting solid was dissolved in 130 ml of methylene chloride, and 65 ml of 1N HCl was added thereto. The organic layer was separated, washed successively with water, saturated sodium bicarbonate and saline, dried over anhydrous MgSO$_4$, and concentrated under a reduced pressure to obtain a mixture of α- and β-phosphate as a solid. The mixture was examined by $^1$H-NMR and found that the α-phosphate:β-phosphate ratio was 1:10.8. The β-phosphate was selectively recrystallized from isopropanol to obtain 15.6 g of the titled compound as a white solid (yield: 83%).

$^1$H-NMR (300 MHz, CDCl$_3$): 4.70-4.40 (m, 3H), 5.90 (m, 1H), 6.08 (t, 1H), 7.70~7.08 (m, 24H), 8.15~8.04 (dd, 4H)

m.p.: 145-147° C.

HPLC purity (area %): α-phosphate anomer 1.29%, β-phosphate anomer 98.71%

Step 3) Preparation of 1-α-bromo-2-deoxy-2,2-difluoro-D-ribofuranosyl-3,5-di-(4-phenyl)benzoate (the Compound of Formula (I))

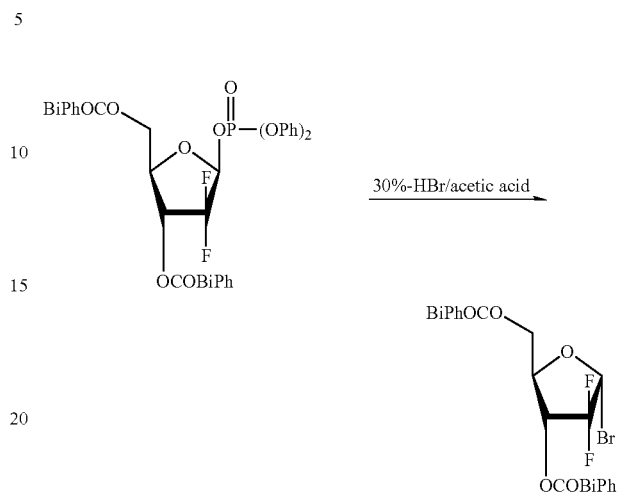

13 g of the compound obtained in Step 2 was dissolved in 83.2 ml of 30% HBr/acetic acid and stirred for 7 hrs at room temperature. 50 ml of ice/water was added thereto and the solid formed was filtered. The filtered solid was a mixture of α- and β-bromo anomers and a $^1$H-NMR analysis showed that the α-brom:β-bromo ratio was 10.9:1. The α-bromo compound was selectively recrystallized from ethanol to obtain 8.45 g of the titled compound as a white solid (yield: 83%).

$^1$H-NMR (300 MHz, CDCl$_3$): 4.89~4.22 (m, 3H), 5.62 (dd, 1H), 6.55 (d, 1H), 7.73~7.42 (m, 14H), 8.63~8.11 (dd, 4H)

m.p.: 151-153° C.

HPLC purity (area %): α-bromo anomer 99.67%, β-bromo anomer 0.33%

Example 3

Preparation of 1-α-bromo-2-deoxy-2,2-difluoro-D-ribofuranosyl-3-benzoyl-5-(4-phenyl)benzoate (In Situ Preparation)

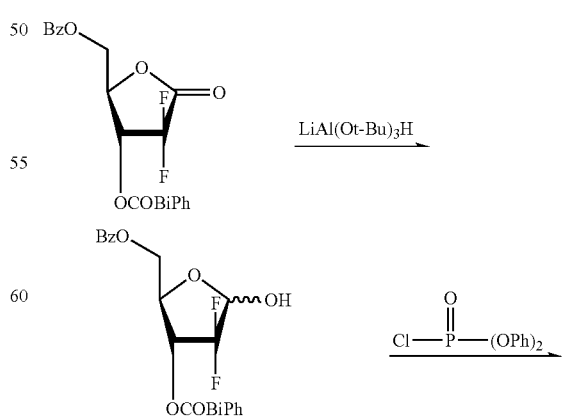

-continued

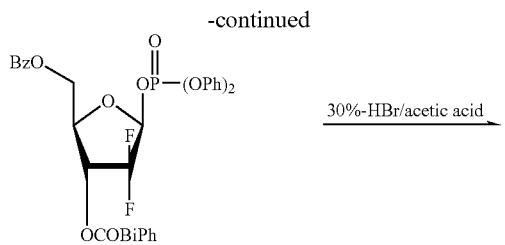

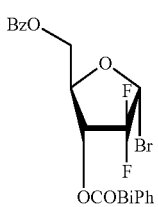

6.5 g of lithium tri-tert-butoxyaluminohydride was dissolved in 100 ml of THF and stirred for 30 minutes at room temperature and cooled to −40° C. 10 g of the compound obtained in Preparation Example 1 dissolved in 50 ml of THF was added dropwise thereto and stirred for 2 hrs at room temperature. Upon the completion of the reaction, 120 ml of 1N HCl was added to the reaction mixture to decompose excess lithium tri-tert-butoxyaluminohydride, the THF and aqueous layers was separated, and the aqueous layer was extracted with 150 ml of diethyl ether. The ether extract was combined with the THF layer, and washed successively with water, saturated sodium bicarbonate and saline. The organic layer was separated, dried over anhydrous MgSO$_4$, filtered, and concentrated under a reduced pressure to obtain 10.5 g of a residue in syrup state.

The resulting residue was dissolved in 100 ml of toluene, and 4.0 ml of triethylamine was added thereto. To the resulting mixture, 6.4 ml of diphenylchlorophosphate dissolved in 30 ml of toluene was added dropwise, followed by stirring 4 hrs at room temperature. Upon the completion of the reaction, 30 ml of 1N HCl was added to the mixture to neutralize residual triethylamine, the toluene and aqueous layers were separated, and the aqueous layer was extracted with 30 ml of diethyl ether. The ether extract was combined with the toluene layer, and washed successively with water, saturated sodium bicarbonate and saline. The organic layer was separated, dried over anhydrous MgSO$_4$, filtered, and concentrated under a reduced pressure to obtain 14.9 g of a mixture of α- and β-phosphate as a syrup. The mixture was examined by $^1$H-NMR and found that the α-phosphate:β-phosphate ratio was 1:10.3.

Subsequently, 57.2 ml of 30% HBr/acetic acid was added to the phosphate mixture and stirred for 7 hrs at room temperature. Upon the completion of the reaction, the mixture was diluted with 280 ml of methylene chloride, poured over ice/water, and the methylene chloride layer was separated. The methylene chloride layer washed successively with ice/water, saturated sodium bicarbonate, and saline. The organic layer was separated, dried over anhydrous MgSO$_4$, filtered, and concentrated under a reduced pressure to obtain a mixture of α- and β-isomers as a solid. The mixture was examined by $^1$H-NMR and found that the α-bromo:β-bromo ratio was 10.5:1. The α-bromo compound was selectively recrystallized from isopropanol to obtain 8.0 g of the titled compound as a white solid (yield: 70%).

$^1$H-NMR and m.p. data were the same as those found in Step 4 of Example 1.

HPLC purity (area %): α-bromo anomer 99.51%, β-bromo anomer 0.48%

Example 4

Preparation of 1-α-iodo-2-deoxy-2,2-difluoro-D-ribofuranosyl-3-benzoyl-5-(4-phenyl)benzoate

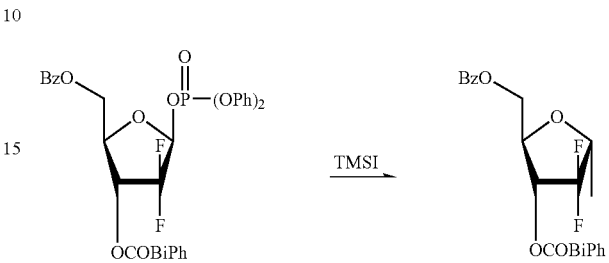

5.6 ml of iodotrimethylsilane was added to 40 ml of methylene chloride, and 1.8 g of the compound obtained in Step 2 of Example 1 was added thereto, and the mixture was stirred for 0.5 hrs at room temperature. The mixture was added dropwise to 100 ml of saturated sodium bicarbonate while cooling over an ice bath, and stirred for 0.5 hrs. The methylene chloride layer was separated, dried over anhydrous MgSO$_4$, and concentrated under a reduced pressure to obtain a mixture of α- and β-isomers as a solid. The mixture was examined by $^1$H-NMR and found that the α-iodo:β-iodo ratio was 14.2:1. The α-iodo compound was selectively recrystallized from isopropanol to obtain 1.36 g of the titled compound as a white solid (yield: 92%).

$^1$H-NMR (300 MHz, CDCl$_3$): 8.24 (d, 2H), 8.06 (d, 2H), 7.74 (d, 2H), 7.66 (d, 2H), 7.64-7.43 (m, 6H), 6.93 (d, 1H), 5.60 (dd, 1H), 4.86~4.68 (m, 3H)

HPLC purity (area %): α-iodo anomer 99.81%, β-iodo anomer 0.18%

Comparative Example 1

Preparation of 1-α-iodo-2-deoxy-2,2-difluoro-D-ribofuranosyl-3,5-dibenzoate

The titled compound was prepared in accordance with the method disclosed in U.S. Pat. No. 5,453,499 as describe below.

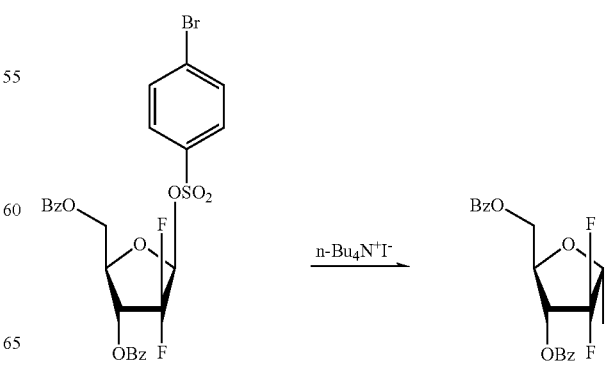

80 ml of tetrahydrofuran and 80 ml of tetrabutylammonium iodide was added to 1 g of 2-deoxy-2,2-difluoro-D-ribofuranosyl-3,5-dibenzoyl-1-β-(p-bromobenzene)sulfonate, and the mixture was refluxed for 3.5 hrs. The resulting mixture comprised a mixture of α-iodo and β-iodo, and a $^1$H-NMR analysis showed that the α-iodo:β-iodo ratio was 10:1.

In order to isolate the α-iodo compound, the mixture was cooled and diluted with dichloromethane and water. The organic layer was separated, washed successively with 1N HCl, sodium carbonate, saturated saline and water, dried over anhydrous MgSO$_4$, and concentrated under a reduced pressure to obtain a residue in a syrup state. The resulting residue was purified by silica gel flash chromatography (toluene/hexane (2:1, v/v)) to obtain 302 mg of the titled compound (yield: 45%).

$^1$H-NMR (300 MHz, CDCl$_3$): 8.12 (m, 4H), 7.72~7.4 (m, 6H), 6.92 (d, 1H), 5.60 (dd, 1H), 4.91~4.62 (m, 3H)

While the invention has been described with respect to the above specific embodiments, it should be recognized that various modifications and changes may be made to the invention by those skilled in the art which also fall within the scope of the invention as defined by the appended claims.

What is claimed is:

1. A 1-α-halo-2,2-difluoro-2-deoxy-D-ribofuranose derivative of formula (I) in a solid form:

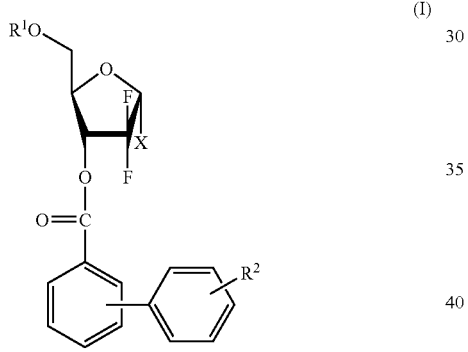

(I)

wherein,
R$^1$ is benzoyl or

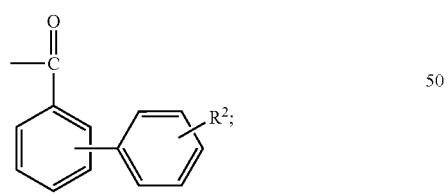

R$^2$ is hydrogen, cyano, halogen, carboalkoxy, nitro, C$_{1-2}$ alkoxy, C$_{1-2}$ alkyl or dialkylamino; and
X is Cl, Br or I.

2. The derivative of claim 1, wherein R$^2$ is hydrogen.

3. The derivative of claim 1, wherein the β-anomer content is 0.5% or less.

4. A method for preparing the 1-α-halo-2,2-difluoro-2-deoxy-D-ribofuranose derivative of formula (I), comprising the steps of
(i) reducing a 1-oxoribose compound of formula (II) to obtain a lactol compound of formula (III);

(ii) reacting the compound of formula (III) with a halophosphate compound of formula (IV) in the presence of a base to obtain a 1-phosphate furanose derivative of formula (V); and (iii) reacting the compound of formula (V) with a halide source, followed by recrystallizing the resulting product to obtain the 1-α-halo-2,2-difluoro-2-deoxy-D-ribofuranose derivative of formula (I):

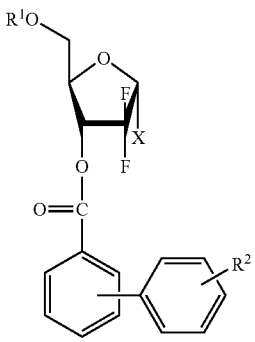

(I)

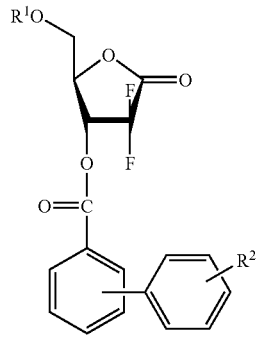

(II)

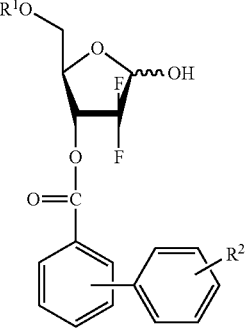

(III)

(IV)

$$X-\overset{O}{\underset{\|}{P}}\cdot(OR^3)_2$$

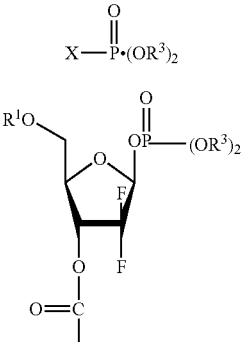

(V)

wherein, $R^1$, $R^2$ and X have the same meanings as defined in claim 1; and $R^3$ is methyl, ethyl or phenyl.

5. The method of claim 4, wherein the base used in step (ii) is selected from the group consisting of pyridine, triethylamine, tributylamine, diisopropylethylamine and methylpiperidine.

6. The method of claim 5, wherein the base used in step (ii) is triethylamine.

7. The method of claim 4, wherein the halide source used in step (iii) is selected from the group consisting of HCl/acetic acid, HBr/acetic acid, HBr/propionic acid, a trialkylsilyl halide, a lithium halide, a sodium halide, a cesium halide, a potassium halide, tetraalkylammonium halide and a mixture thereof.

8. The method of claim 7, wherein the halide source used in step (iii) is selected from the group consisting of 30% HBr/acetic acid, 30% HBr/propionic acid, tetrabutylammonium iodide, tetrabutylammonium bromide, trimethylsilyl iodide, trimethylsilyl bromide, trimethylsilyl chloride and a trimethylsilyl chloride-lithium bromide mixture.

9. The method of claim 4, wherein the recrystallization in step (iii) is carried out using a solvent selected from the group consisting of methanol, ethanol, isopropanol, acetonitrile, water and a mixture thereof.

10. The method of claim 9, wherein the recrystallization in step (iii) is carried out using isopropanol or an isopropanol-water mixture.

11. The method of claim 4, wherein the derivative of formula (I) is obtained in a purity of 99.5% or more.

12. A 1-phosphate furanose derivative of formula (V):

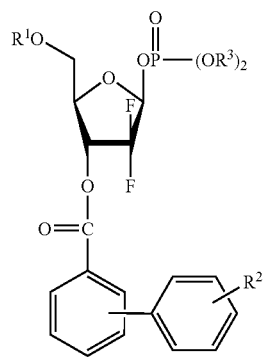

(V)

wherein,
$R^1$ is benzoyl or

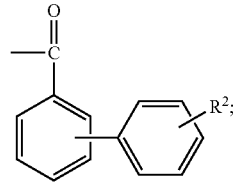

$R^2$ is hydrogen, cyano, halogen, carboalkoxy, nitro, $C_{1-2}$ alkoxy, $C_{1-2}$ alkyl or dialkylamino; and
$R^3$ is methyl, ethyl or phenyl.

* * * * *